United States Patent [19]
Riedel et al.

[11] Patent Number: 6,133,173
[45] Date of Patent: Oct. 17, 2000

[54] NONWOVEN COHESIVE WRAP

[75] Inventors: John E. Riedel, St. Paul; Eugene G. Joseph, Vadnais Heights, both of Minn.; Roberta C. Harper, St. Joseph Township, Wis.

[73] Assignee: 3M Innovative Properties Company, St. Paul, Minn.

[21] Appl. No.: 08/980,921

[22] Filed: Dec. 1, 1997

[51] Int. Cl.$^7$ .............................. B32B 27/00; D04H 1/00; A61F 13/02

[52] U.S. Cl. ......................... 442/400; 442/151; 442/328; 442/341; 442/351

[58] Field of Search .................................... 442/400, 151, 442/328, 341, 347, 351, 361; 428/343, 356, 355 AC

[56] References Cited

U.S. PATENT DOCUMENTS

| | | | |
|---|---|---|---|
| 3,121,021 | 2/1964 | Copeland | 117/122 |
| 3,480,502 | 11/1969 | Schrenk | 156/271 |
| 3,487,505 | 1/1970 | Chisholm et al. | 18/13 |
| 3,825,379 | 7/1974 | Lohkamp et al. | 425/72 |
| 3,849,241 | 11/1974 | Butin et al. | 161/169 |
| 3,908,650 | 9/1975 | Dunshee et al. | 128/156 |
| 3,954,697 | 5/1976 | McConnell et al. | 526/350 |
| 3,971,373 | 7/1976 | Braun | 128/146.2 |
| 4,024,312 | 5/1977 | Korpman | 428/343 |
| 4,072,812 | 2/1978 | McConnell et al. | 526/348.2 |
| 4,210,570 | 7/1980 | Trotter et al. | 260/33.6 |
| 4,217,428 | 8/1980 | McConnell et al. | 525/191 |
| 4,264,756 | 4/1981 | Trotter et al. | 526/348.2 |
| 4,379,201 | 4/1983 | Heilmann et al. | 428/345 |
| 4,554,324 | 11/1985 | Husman et al. | 525/301 |
| 4,619,979 | 10/1986 | Kotnour et al. | 526/88 |
| 4,729,371 | 3/1988 | Krueger et al. | 128/206 |
| 4,737,559 | 4/1988 | Kellen et al. | 526/291 |
| 4,789,699 | 12/1988 | Kiefffer et al. | 524/271 |
| 4,797,318 | 1/1989 | Brooker et al. | 428/283 |
| 4,843,134 | 6/1989 | Kotnour et al. | 526/318.4 |
| 4,874,447 | 10/1989 | Hazelton et al. | 156/167 |
| 5,061,170 | 10/1991 | Allen et al. | 425/197 |
| 5,176,952 | 1/1993 | Joseph et al. | 428/284 |
| 5,190,812 | 3/1993 | Joseph et al. | 428/297 |
| 5,207,970 | 5/1993 | Joseph et al. | 264/518 |
| 5,230,701 | 7/1993 | Meyer et al. | 442/400 X |
| 5,232,770 | 8/1993 | Joseph | 428/284 |
| 5,238,733 | 8/1993 | Joseph et al. | 428/284 |
| 5,248,455 | 9/1993 | Joseph et al. | 264/6 |
| 5,258,220 | 11/1993 | Joseph | 428/284 |
| 5,302,447 | 4/1994 | Ogata et al. | 442/400 X |
| 5,382,400 | 1/1995 | Pike et al. | 264/168 |
| 5,421,941 | 6/1995 | Allen et al. | 156/244.11 |
| 5,462,538 | 10/1995 | Korpman | 604/372 |
| 5,506,279 | 4/1996 | Babu et al. | 522/34 |
| 5,516,581 | 5/1996 | Kreckel et al. | 428/317.3 |
| 5,601,851 | 2/1997 | Terakawa | 425/72.2 |
| 5,613,942 | 3/1997 | Lucast et al. | 602/52 |
| 5,629,079 | 5/1997 | Battles et al. | 442/60 |
| 5,637,646 | 6/1997 | Ellis | 525/309 |
| 5,843,057 | 12/1998 | McCormack | 442/400 X |

FOREIGN PATENT DOCUMENTS

| | | | |
|---|---|---|---|
| 2129496 | 10/1995 | Canada | D04H 1/56 |
| 0 341 875 A2 | 4/1989 | European Pat. Off. | D04H 1/56 |
| 0 420 256 A2 | 9/1990 | European Pat. Off. | B29C 67/14 |
| 0 432 763 A1 | 12/1990 | European Pat. Off. | D04H 1/56 |
| 0 579 883 A1 | 7/1992 | European Pat. Off. | D04H 1/42 |
| 0 586 937 A1 | 8/1993 | European Pat. Off. | D04H 13/00 |
| 0 658 351 A1 | 12/1994 | European Pat. Off. | A61L 15/58 |
| 0 674 890 A2 | 3/1995 | European Pat. Off. | A61F 13/02 |
| 0 702 994 A1 | 3/1996 | European Pat. Off. | B01D 39/16 |
| 749 756 A2 | 6/1996 | European Pat. Off. | A61L 15/58 |
| WO 92/16361 | 9/1991 | WIPO | B23B 3/02 |
| WO 96/07522 | 3/1996 | WIPO | B29B 13/02 |
| WO 96/16625 | 6/1996 | WIPO | A61F 13/15 |
| WO 97/02375 | 1/1997 | WIPO | D01F 8/06 |
| WO 97/23267 | 7/1997 | WIPO | B01D 39/16 |

OTHER PUBLICATIONS

Stuart, R.K. et al., "Hot–Melt Pressure Sensitive Adhesives Based on Polyofelins", Technical Seminar Proceedings, Tech XI, Advances in Pressure Sensitive Tape Technology, May 4–6, 1988, Itasca, Illinois, pp. 93–113.

Wente, Van A., "Superfine Thermoplastic Fibers", *Industrial Engineering Chemistry*, vol. 48, pp. 1342–1346 (undated).

Wente et al., "Manufacture of Superfine Organic Fibers", *Report No. 4364 of the Naval Research Laboratories*, published May 25, 1954.

Jap Patent Abst 01308472; Nitto Denko Corp., published Dec. 1989.

*Primary Examiner*—Daniel Zirker
*Attorney, Agent, or Firm*—Gary L. Griswold; Robert W. Sprague; William J. Bond

[57] ABSTRACT

A dispensable nonwoven cohesive wrap that is generally dispensed from a self-wound roll. The nonwoven cohesive wrap comprises mutually entangled fibers at least some of which are pressure-sensitive adhesive fibers. The cohesive wrap also generally has a basis weight of from 40 to 200 grams/m$^2$, a tensile strength of at least 100 grams/2.5 cm and a T-peel from itself of from 1 to 30 grams/2.5 cm. The wrap is preferably a single layer material without a separate adhesive coating or release coating where the adhesive fibers extend through the entire depth dimension of the wrap, such that a portion of the adhesive fibers are on both faces of the wrap, and preferably are uniformly distributed across the length and width dimensions of the wrap.

36 Claims, No Drawings

NONWOVEN COHESIVE WRAP

The present invention relates to pressure-sensitive adhesive, cohesive wraps particularly useful for medical and sport applications.

Elastomeric pressure-sensitive adhesive tapes designed particularly for medical applications are known, such as described in U.S. Pat. No. 4,024,312. This patent describes an elastomeric film backing formed preferably with a linear or radial ABA-block copolymer which preferably contains from 85–200 parts of resin to 100 parts of elastomer. The preferred block copolymer described is a polyisoprene polystyrene block copolymer or a polybutadiene polystyrene block copolymer. These elastomeric film backings are formed to a tape with a rubber resin adhesive layer, similarly formed with block copolymers such as polystyrene polyisoprene with a polyisoprene compatible tackifier. Problems with this tape include the fact that it is not breathable, has a tendency to block in a roll form, and the tackifying resin tends to migrate from the adhesive layer to the elastomeric backing. Further, the tape is difficult to dispense in that an elastic film backing is not easily tearable. Also, in order to be easily removed from the skin, it is necessary to elongate the backing in a plane parallel with the skin which is often difficult and generally not easily remembered by the end consumer.

Porous medical tapes are known, for example, from U.S. Pat. Nos. 3,908,650; 3,121,021; and 5,613,942, which propose various types of nonwoven or woven fibrous backings. Adhesives are coated in various manners onto the fibrous backings in each of the patents so as to provide a conventional form of tape product. These types of porous medical tapes are desired for many applications where the adhesive tape is generally designed to adhere directly to the skin. However, due to the nature of these porous tapes, they are generally relatively complicated to form and require relatively aggressive adhesives. For example, problems that generally need to be addressed with these tapes include: the backing must have sufficient integrity so that fibers are not pulled free by the adhesive layer on the overlying wrap of tape on a roll; the adhesive must be firmly anchored to one face of the backing, but release from the opposite face of the backing; adhesive and release coatings generally cannot migrate from one face of the porous backing to the opposite face; the adhesive must not coalesce into a continuous film layer; the adhesive should bond well to skin, even if moisture is present; etc. These objectives are often conflicting and as such difficult to resolve simply.

Generally, the adhesives used in these porous medical tapes are acceptable for short term usage, but can cause problems with sensitive skin types and/or with extended periods of use. As such, there is a need for materials to protect the skin from these adhesives, particularly for athletes or others where there is a need for repeated retaping of a given area of skin.

There is known in the art the use of a thin skived polyurethane foam to protect the skin from contact with adhesives used in medical or sport tape products. This polyurethane foam has a slight cling to itself and may be wrapped around an appendage with a slight degree of stretch. The skived polyurethane foam material is used as a tape underwrap providing a surface for a medical or athletic tape to be wrapped around a wearer and subsequently removed without issues of adhesive transfer to the skin or skin rashes which can be associated with extended skin contact with continuous tape adhesives layers. However, this material is deficient in self adhesion such that it easily unwinds when there is movement prior to tape application. Polyurethane foam also can be difficult to adhere due to the low outer surface area. Additionally, polyurethane foam is somewhat thick, reducing the effectiveness of the overwrap tape in protecting the skin and/or restricting motion. Often, a spray adhesive is used to help adhere the polyurethane foam to itself or to other surfaces. However, this procedure can be time consuming and costly, and the spray adhesive can be messy and leave an undesirable residue on the skin.

The present invention is directed at providing a cohesive sheet material or tape which can be wrapped around an appendage and adhere to itself readily, yet be easily removed, which material also has high levels of breathability, has a low profile, is easily dispensable or tearable and adheres well to conventional medical or sport tapes.

BRIEF SUMMARY OF THE INVENTION

The invention relates to a dispensable nonwoven cohesive wrap that is generally dispensed from a self-wound roll. The nonwoven cohesive wrap comprises mutually entangled fibers at least some of which are pressure-sensitive adhesive fibers. The cohesive wrap also generally has a basis weight of from 40 to 200 grams/m$^2$, a tensile strength of at least 100 grams/2.5 cm and a T-peel from itself of from 1 to 30 grams/2.5 cm. The wrap is preferably a single layer material without a separate adhesive coating or release coating where the adhesive fibers extend through the entire depth dimension of the wrap, such that a portion of the adhesive fibers are on both faces of the wrap, and preferably are uniformly distributed across the length and width dimensions of the wrap.

DESCRIPTION OF THE PREFERRED EMBODIMENTS

The invention nonwoven cohesive wrap is formed from coherent fibers including at least in part pressure-sensitive adhesive fibers which are intimately entangled each with the other in the form of a coherent breathable nonwoven web. Suitable pressure-sensitive adhesive fibers can be formed as melt blown microfibers using the apparatus discussed, for example, in Wente, Van A., "Superfine Thermoplastic Fibers", *Industrial Engineering Chemistry*, Vol. 48, pages 1342–1346, Wente, Van A. et al., "Manufacture of Superfine Organic Fibers", Report No. 4364 of the Navel Research Laboratories, published May 25, 1954, and in U.S. Pat. Nos. 3,849,241; 3,825,379; and others. These microfine fibers are termed melt blown fibers and are generally substantially continuous and form into a coherent web between the exit die orifice and a collecting surface by entanglement of the microfibers due in part to the turbulent airstream in which the fibers are entrained. Further, suitable pressure-sensitive adhesive fibers used in the invention cohesive wrap can be formed by other conventional melt spinning processes, such as spunbond processes. Generally, the adhesive fibers are 50 microns or less in diameter when formed by melt spinning type processes and preferably are greater than 10 microns in diameter.

The invention cohesive wrap preferably also comprises non-pressure-sensitive adhesive fibrous material intimately commingled with the pressure-sensitive adhesive fibers to provide the wrap as a whole with suitable tensile strength, breathability, and cohesive properties. The commingled pressure-sensitive adhesive fibers or microfibers and non-pressure-sensitive adhesive fibrous material can be present in separate individual fibers or the pressure-sensitive adhesive fibers or microfibers and the non-pressure-sensitive material can form distinct regions in a conjugate fiber and/or be part of a blend. For example, conjugate fibers can be in the form of two or more layered fibers, sheath-core fiber arrangements or in "island in the sea" type fiber structures. In this case, one component layer would comprise the pressure-sensitive adhesive fiber or microfiber and a second component layer would comprise the non-pressure-sensitive adhesive fibrous material. Generally with any form of multicomponent conjugate fibers, the pressure-sensitive adhesive fiber component will provide at least a portion of the exposed outer surface of the multicomponent conjugate fiber. Preferably, the individual components of the multicomponent conjugate fibers will be present substantially continuously along the fiber length in discrete zones, which zones preferably extend along the entire length of the fibers. The individual fibers generally are of a fiber diameter of less than 100 microns, preferably less than 50 microns or 25 microns for microfibers.

Conjugate fibers can be formed, for example, as a multilayer fiber as described, for example, in U.S. Pat. Nos. 5,238,733; or 5,601,851. Multilayered and sheath-core melt blown microfibers are described, for example, in U.S. Pat. No. 5,238,733, the substance of which is incorporated herein by reference in its entirety. This patent describes providing a multicomponent melt blown microfiber web by feeding two separate flow streams of polymer material into a separate splitter or combining manifold. The split or separated flow streams are generally combined immediately prior to the die or die orifice. The separate flow streams are preferably established into melt streams along closely parallel flow paths and combined where they are substantially parallel to each other and the flow path of the resultant combined multilayered flow stream. This multilayered flow stream is then fed into the die and/or die orifices and through the die orifices. Air slots are disposed on either side of a row of die orifices directing uniform heated air at high velocities at the extruded multicomponent melt streams. The hot high velocity air draws and attenuates the extruded polymeric material which solidifies after traveling a relatively short distance from the die. The high velocity air becomes turbulent between the die and the collector surface causing the melt blown fibers entrained in the airstream to mutually entangle and form a coherent nonwoven web. The either solidified or partially solidified fibers are then collected on a surface by known methods. Also, other fibers and/or particulates can be fed into this turbulent airstream thereby getting incorporated into the forming coherent nonwoven web. This can be done, for example, by using a macrodropper, a second fiber forming die or other known methods.

Alternatively, conjugate fibers can be formed by a spunbond process such as described in U.S. Pat. No. 5,382,400 where separate polymer flow streams are fed via separate conduits to a spinneret for producing conjugate fibers of a conventional design. Generally, these spinnerets include a housing containing a spin pack with a stack of plates which form a pattern of openings arranged to create flow paths for directing the separate polymer components separately through the spinneret. The spinneret can be arranged to extrude the polymer vertically or horizontally in one or more rows of fibers.

An alternative arrangement for forming melt blown conjugate fibers is described for example, in U.S. Pat. No. 5,601,851. The polymer flow streams are separately fed to each individual die orifice by the use of grooves cut in a distributing and/or separating plate. This arrangement can be used to separately extrude different polymers from different individual orifices to provide separate distinct fibers which form a coherent entangled web having a substantially uniform distribution of the differing fibers. By feeding two, separate polymers to an individual die orifice a conjugate fiber can be formed. The apparatus described is suitably used in a melt blowing type arrangement where the die orifices are formed in a row along the die.

The pressure-sensitive adhesive component comprises an extrudable pressure-sensitive adhesive suitable for melt blowing (generally this requires the adhesive to have an apparent viscosity of from 150 to 800 poise under melt-processing conditions, measured by a capillary rheometer), fiber spinning or spunbond processing. With conjugate fibers or coformed fibers of different polymers or blends formed from a single die or spinneret, the viscosities of the separate polymer flowstreams should be fairly closely matched for uniform fiber and web formation, but this is not required. Generally matching viscosities will ensure more uniformity in the conjugate fibers formed in terms of minimizing polymer mixing, which mixing can result in fiber breakage and formation of shot (small particulate polymer material), and lower web tensile properties. However, the presence of discontinuous fibers or shot is not necessarily undesirable as long as the nonwoven wrap has the desired overall tensile and web or wrap cohesive strength.

The particular pressure-sensitive adhesive used in forming discrete pressure-sensitive adhesive fibers, conjugate fibers or blends (in either discrete or conjugate fibers) depends on the desired end use and the non-pressure-sensitive adhesive material polymers selected in the case of polymer blends or conjugate fibers. The pressure-sensitive adhesive is generally any hot melt extrudable copolymer or composition having a viscosity in the melt phase suitable for fiber forming by melt processing or in the solution phase for solution spun fibers. Suitable classes of pressure-sensitive adhesives include acrylate adhesives, polyalphaolefin adhesives, rubber resin adhesives or the like.

Suitable rubber resin adhesives would include those formed using a tackified elastomer where a preferred elastomer is an A-B type block copolymer wherein the A blocks and B blocks are configured in linear (e.g. diblock or triblock copolymer), radial or star configurations. The A block is formed of a mono-alkenylarene, preferably a polystyrene block having a molecular weight between 4000 and 50,000, preferably between 7000 and 30,000. The A block content is preferably about 10 to 50 weight percent, preferably about 10 to 30 weight percent of the block copolymer. Other suitable A blocks may be formed from alpha-methylstyrene, t-butyl-styrene and other ring alkylated styrenes, as well as mixtures thereof. The B block is formed of an elastomeric conjugated diene, generally polyisoprene, polybutadiene or copolymers thereof having an average molecular weight from about 5000 to about 500,000, preferably from about 50,000 to about 200,000. The B block dienes can also be hydrogenated. The B block content is generally 90 to 50 percent, preferably 90 to 70 percent by weight. The tackifying components for the elastomer based adhesives generally comprise solid tackifying resin and/or a liquid tackifier or plasticizer. Preferably, the tackifying resins are selected from the group of resins at least partially compatible with the polydiene B block portion of the elastomer. Although not preferred, generally a relatively minor amount of the tackifying resin can include resins compatible with the A block, which when present are generally termed end block reinforcing resins. Generally, end block resins are formed from aromatic monomer species. Suitable liquid tackifiers or plasticizers for use in the adhesive composition include napthenic oils, paraffin oils, aromatic oils, mineral oils or low molecular weight rosin esters, polyterpenes and C-5 resins. Some suitable B-block compatible solid tackifying resins include C-5 resins, resin esters, polyterpenes and the like.

The tackifier portion of the pressure-sensitive adhesive generally comprises from 20 to 300 parts per 100 parts of the elastomer phase. Preferably, this is predominately solid tackifier, however, from 0 to 25 weight percent, preferably 0 to 10 weight percent of the adhesive composition can be liquid tackifier and/or plasticizer.

Suitable rubber resin adhesives for melt blown processing are discussed in EP 658351 which exemplifies melt-blown fibrous synthetic rubber resin type adhesives used in a disposable absorbent article to either immobilize particulate sorbents or used as a pressure-sensitive adhesive attachment (e.g., for a sanitary napkin). Suitable adhesives exemplified are styrene-isoprene-styrene triblock block copolymer based, where the copolymer has coupling efficiencies ranging from 42 to 65 percent (e.g., 58 to 35 percent polystyrene-polyisoprene diblock material would be present), tackified with C-5 hydrocarbon resins (WINGTACK PLUS and WINGTACK 10, available from Goodyear Chemical) and stabilized with antioxidants.

Generally, depending on the fiber formation process, suitable antioxidants and heat stabilizers could be used in the present invention to prevent the degradation of the adhesive during the fiber forming process or in use. Also, other conventional additives could be used such as UV absorbents, pigments, particulates, staple fibers or the like.

Suitable poly(acrylates) are derived from: (A) at least one monofunctional alkyl (meth)acrylate monomer (i.e., alkyl acrylate and alkyl methacrylate monomer); and (B) at least one monofunctional free-radically copolymerizable reinforcing monomer. The reinforcing monomer has a homopolymer glass transition temperature ($T_g$) higher than that of the alkyl (meth)acrylate monomer and is one that increases the glass transition temperature and modulus of the resultant copolymer. Monomers A and B are chosen such that a copolymer formed from them is extrudable and capable of forming fibers. Herein, "copolymer" refers to polymers containing two or more different monomers, including terpolymers, tetrapolymers, etc.

Preferably, the monomers used in preparing the pressure-sensitive adhesive copolymer fibers of the present invention include: (A) a monofunctional alkyl (meth)acrylate monomer that, when homopolymerized, generally has a glass transition temperature of no greater than about 0° C.; and (B) a monofunctional free-radically copolymerizable reinforcing monomer that, when homopolymerized, generally has a glass transition temperature of at least about 10° C. The glass transition temperatures of the homopolymers of monomers A and B are typically accurate to within ±5° C. and are measured by differential scanning calorimetry.

Monomer A, which is a monofunctional alkyl acrylate or methacrylate (i.e., (meth)acrylic acid ester), contributes to the flexibility and tack of the copolymer. Preferably, monomer A has a homopolymer $T_g$ of no greater than about 0° C. Preferably, the alkyl group of the (meth)acrylate has an average of about 4 to about 20 carbon atoms, and more preferably, an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylate (i.e., poly(ethylene/propylene oxide) mono-(meth)acrylate) macromers (i.e., macromolecular monomers), polymethylvinyl ether mono (meth)acrylate macromers, and ethoxylated or propoxylated nonyl-phenol acrylate macromers. The molecular weight of such macromers is typically about 100 grams/mole to about 600 grams/mole, and preferably, about 300 grams/mole to about 600 grams/mole. Combinations of various monofunctional monomers categorized as an A monomer can be used to make the copolymer used in making the fibers of the present invention.

Monomer B, which is a monofunctional free-radically copolymerizable reinforcing monomer; increases the glass transition temperature of the copolymer. As used herein, "reinforcing" monomers are those that increase the modulus of the adhesive, and thereby its strength. Preferably, monomer B has a homopolymer $T_g$ of at least about 10° C. More preferably, monomer B is a reinforcing monofunctional (meth)acrylic monomer, including an acrylic acid, a methacrylic acid, an acrylamide, and an acrylate. Examples of monomer B include, but are not limited to, acrylamides, such as acrylamide, methacrylamide, N-methyl acrylamide, N-ethyl acrylamide, N-methylol acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dimethylol acrylamide, N,N-dihydroxyethyl acrylamide, t-butyl acrylamide, dimethylaminoethyl acrylamide, N-octyl acrylamide, and 1,1,3,3-tetramethylbutyl acrylamide. Other examples of monomer B include acrylic acid and methacrylic acid, itaconic acid, crotonic acid, maleic acid, fumaric acid, 2,2-(diethoxy)ethyl acrylate, hydroxyethyl acrylate or methacrylate, 2-hydroxypropyl acrylate or methacrylate, methyl methacrylate, isobutyl acrylate, n-butyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl pyrrolidone, and N-vinyl caprolactam. Combinations of various reinforcing monofunctional monomers categorized as a B monomer can be used to make the copolymer used in making the fibers of the present invention.

The acrylate copolymer is preferably formulated to have a resultant $T_g$ of less than about 25° C. and more preferably, less than about 0° C. Such acrylate copolymers preferably include about 60 parts to about 98 parts per hundred of at least one alkyl (meth)acrylate monomer and about 2 parts to about 40 parts per hundred of at least one copolymerizable reinforcing monomer. Preferably, the acrylate copolymers have about 85 parts to about 98 parts per hundred or at least one alkyl (meth)acrylate monomer and about 2 parts to about 15 parts of at least one copolymerizable reinforcing monomer.

A crosslinking agent can be used if so desired to build the molecular weight and the strength of the copolymer, and hence improve the integrity and shape of the fibers. Preferably, the crosslinking agent is one that is copolymerized with monomers A and B. The crosslinking agent may produce chemical crosslinks (e.g., covalent bonds). Alternatively, it may produce physical crosslinks that result, for example, from the formation of reinforcing domains due to phase separation or acid base interactions. Suitable crosslinking agents are disclosed in U.S. Pat. Nos. 4,379,201 (Heilman), 4,737,559 (Kellen), 5,506,279 (Babu et al.) and 4,554,324 (Husman).

This crosslinking agent is preferably not activated towards crosslinking until after the copolymer is extruded and the fibers are formed. Thus, the crosslinking agent can be a photocrosslinking agent, which, upon exposure to ultraviolet radiation (e.g., radiation having a wavelength of about 250 nanometers to about 400 nanometers), causes the copolymer to crosslink. Preferably, however, the crosslinking agent provides crosslinking, typically, physical crosslinking, without further processing. Physical crosslinking can occur through phase separation of domains which produces thermally reversible crosslinks. Thus, acrylate copolymers prepared from a crosslinker that provides reversible physical crosslinking are particularly advantageous in the preparation of fibers using a melt process.

Preferably, the crosslinking agent is (1) an acrylic crosslinking monomer, or (2) a polymeric crosslinking material having a copolymerizable vinyl group. More preferably the crosslinking agent is a polymeric material having a copolymerizable vinyl group. Preferably, each of these monomers is a free-radically polymerizable crosslinking agent capable of copolymerizing with monomers A and B. Combinations of various crosslinking agents can be used to make the copolymer used in making the fibers of the present invention. It should be understood, however, that such crosslinking agents are optional.

The acrylic crosslinking monomer is preferably one that is copolymerized with monomers A and B and generates free radicals in the polymer backbone upon irradiation of the polymer. An examples such a monomer is an acrylated benzophenone as described in U.S. Pat. No. 4,737,559 (Kellen et al.).

The polymeric crosslinking materials that have a copolymerizable vinyl group is preferably represented by the general formula X—(Y)$_n$—Z wherein: X is a copolymerizable vinyl group; Y is a divalent linking group where n can be zero or one; and Z is a monovalent polymeric moiety having a T$_g$ greater than about 20° C. and a weight average molecular weight in the range of about 2,000 to about 30,000 and being essentially unreactive under copolymerization conditions. Particularly preferred vinyl-terminated polymeric monomers useful in making the microfibers of the present invention are further defined as having: an X group which has the formula HR$^1$C=CR$^2$— wherein R$^1$ is a hydrogen atom or a COOH group and R$^2$ is a hydrogen atom or a methyl group; a Z group which has the formula —{C(R$^3$)(R$^4$)—CH$_2$}$_n$—R$^5$ wherein R$^3$ is a hydrogen atom or a lower (i.e., C$_1$–C$_4$) alkyl group, R$^5$ is a lower alkyl group, n is an integer from 20 to 500, and R$^4$ is a monovalent radical selected from the group consisting of —C$_6$H$_4$R$^6$ and —CO$_2$R$^7$ wherein R$^6$ is a hydrogen atom or a lower alkyl group and R$^7$ is a lower alkyl group.

Such vinyl-terminated polymeric crosslinking monomers are sometimes referred to as macromolecular monomers (i.e., "macromers"). Once polymerized with the (meth) acrylate monomer and the reinforcing monomer, a vinyl-terminated polymeric monomer of this type forms a copolymer having pendant polymeric moieties which tend to reinforce the otherwise soft acrylate backbone, providing a substantial increase in the shear strength of the resultant copolymer adhesive. Specific examples of such crosslinking polymeric materials are disclosed in U.S. Pat. No. 4,554,324 (Husman et al.).

If used, the crosslinking agent is used in an effective amount, by which is meant an amount that is sufficient to cause crosslinking of the pressure-sensitive adhesive to provide the desired final adhesion properties to the substrate of interest. Preferably, if used, the crosslinking agent is used in an amount of about 0.1 part to about 10 parts, based on the total amount of monomers.

If a photocrosslinking agent has been used, the adhesive in the form of fibers can be exposed to ultraviolet radiation having a wavelength of about 250 nm to about 400 nm. The radiant energy in this preferred range of wavelength required to crosslink the adhesive is about 100 milliJoules/centimeter$^2$ (mJ/cm$^2$) to about 1,500 mJ/cm$^2$, and more preferably, about 200 mJ/cm$^2$ to about 800 mJ/cm$^2$.

The acrylate pressure-sensitive adhesives of the present invention can be synthesized by a variety of free-radical polymerization processes, including solution, radiation, bulk, dispersion, emulsion, and suspension polymerization processes. Bulk polymerization methods, such as the continuous free radical polymerization method described in U.S. Pat. Nos. 4,619,979 or 4,843,134 (both to Kotnour et al.), the essentially adiabatic polymerization methods using a batch reactor described in U.S. Pat. No. 5,637,646 (Ellis), and the methods described for polymerizing packaged pre-adhesive compositions described in International Patent Application No. WO 96/07522, may also be utilized to prepare the polymer used in the preparation of the fibers of the present invention.

The acrylate pressure-sensitive adhesive compositions of the present invention can include conventional additives such as tackifiers (wood rosin, polyesters, etc.), plasticizers, flow modifiers, neutralizing agents, stabilizers, antioxidants, fillers, colorants, and the like, as long as they do not interfere in the fiber-forming melt process. Initiators that are not copolymerizable with the monomers used to prepare the acrylate copolymer can also be used to enhance the rate of polymerization and/or crosslinking. These additives are incorporated in amounts that do not materially adversely affect the desired properties of the pressure-sensitive adhesives or their fiber-forming properties. Typically, they can be mixed into these systems in amounts of about 0.05 weight percent to about 25 weight percent, based on the total weight of the composition.

Suitable polyolefin adhesives would include tackified polyolefin elastomer type adhesives, or amorphous polyalphaolefin polymers suitable for forming hot melt pressure-sensitive adhesives with or without added tackifier. Such amorphous polyalphaolefins are generally copolymers of a C$_3$ to C$_5$ linear alpha-olefin(s) and a higher alpha-olefin(s) (generally C$_6$ to C$_{10}$). Preferred are copolymers of polyolefins with polyhexene, polyheptene, polyoctene, polynonene and/or polydecene. Such amorphous polyalphaolefins are described in U.S. Pat. Nos. 4,264,756; 3,954,697; and 4,072,812 where the amorphous polyalphaolefin copolymers can be used without added tackifiers to directly form a pressure-sensitive adhesive. These amorphous copolymers generally have from 40 to 60 mole percent of the higher alphaolefin comonomer(s). However, suitable compatible tackifying resins and plasticizing oils can be used which generally correspond to those used to tackify the synthetic A-B type block copolymer elastomers described above. For example, suitable compatible liquid or solid tackifiers would include hydrocarbon resins, such as polyterpenes, C-5 hydrocarbon resins, or polyisoprenes, also resin esters of aromatic or aliphatic acids would be suitable. If these tackifiers are used in sufficient amounts, the higher alphaolefin content can be as low as 15 mole percent and still suitable pressure-sensitive adhesives can be formed.

Suitable non-adhesive materials for use in forming conjugate fibers, for use in blends with the pressure-sensitive adhesive or for use as separate fibers, include polyolefins, polyesters, polyalkylenes, polyamides, polystyrenes, polyarylsulfones, polydienes or polyurethanes; these materials are preferably extensible or slightly elastomeric, but could be elastomeric. Preferred are extensible or slightly elastomeric polyolefins such as polyethylenes, polypropylenes, ethylene-propylene copolymers, ethylene/vinyl acetate copolymers, or metallocene-type polyethylenes having a density of greater than 0.87 grams/cm$^3$. Suitable elastomeric materials would include metallocene-type polyethylene copolymers (apparent density less than 0.87 grams/cm$^3$); polyurethanes (e.g., "MORTHANE"); polyolefin elastomers (e.g., ethylene/propylene/diene elastomers); A-B block copolymers, as described above, having A blocks formed of poly (vinyl arenes) such as polystyrene and B blocks formed of conjugated dienes such as isoprene, butadiene, or hydrogenated versions thereof (e.g., "KRATON" elastomers available from Shell Chemical Co.); polyetheresters (such as "ARNITAL", available from Akzo Plastics Co.); or polyether block amides (such as "PEBAX", available from Atochem Co.). Blends of elastomers, blends of nonelastomers or blends of both elastomers and nonelastomers can also be used for the non-pressure-sensitive adhesive fibers, conjugate fibers or in suitable blend fibers.

The non-pressure-sensitive adhesive material in fibrous form generally comprises 5 to 95 percent of the basis weight of the fibers in the nonwoven cohesive wrap, preferably 10 to 90 percent. The non-pressure-sensitive material if present solely in the form of a blend with the pressure-sensitive adhesive material is preferably from 20 to 80 percent of the basis weight of the fibers forming the cohesive wrap, preferably of the substantially continuous fibers forming the cohesive wrap. However, the use of blends of the non adhesive material with the pressure-sensitive adhesive material decreases the adhesion of the cohesive wrap to itself. Higher levels of self adhesion or cohesion can be obtained where the pressure-sensitive adhesive component is present without significant levels of non-adhesive polymer material in a blend, for example, where the non-adhesive polymer is in discrete or conjugate fiber form. Where the non-pressure-sensitive adhesive material is present as a discrete fiber, these fibers are generally intimately commingled with the pressure-sensitive adhesive fibers. If the non-pressure-sensitive fibrous component is present as commingled fibers, these fibers can be formed from the same die as per U.S. Pat. No. 5,601,851 above, or in a separate die which could direct the non-pressure-sensitive adhesive fibers directly, or subsequently, into the fiber stream containing the pressure-sensitive adhesive fibers prior to collection of either fiber on a collection surface. The use of multiple dies for forming commingled fibers is known in the art.

The invention nonwoven cohesive wrap is preferably at least slightly elastomeric such that it will actively engage the wearer. This can be provided in part by the elastomeric component of the pressure-sensitive adhesive and/or by providing a slightly elastomeric or elastomeric non-pressure-sensitive fibrous component. The cohesive wrap generally should exhibit an elastic recovery force(as defined in the examples) at low elongation levels, generally at about 50 percent, of at least 50 grams/2.5 cm. Further, the cohesive wrap should generally recover by at least 40 percent at 50 percent elongation for most uses. For use as a sports wrap or tape underwrap, the invention cohesive wrap should generally recover by at least 80 percent, preferably by at least 90 percent at 50 percent elongation. The force(as defined in the examples) at 50 percent elongation for general use should be from 75 to 1000 grams/2.5 cm, for use as a tape underwrap, slightly lower strength within the range is desired so that the material can be easily extended and torn by hand. Tape underwraps generally should have a force at 50 percent elongation in the range of 150 to 700, preferably 200 to 400 grams/2.5 cm. Similarily, for general uses, the invention wrap can have a tensile strength (as defined in the examples) of from 100 to 2000 grams/2.5 cm and an elongation at break (as defined in the examples) of from 100 to 900 percent. However, for use as a tape underwrap, lower strength and elongation is desired. Preferably, a tape underwrap should have a tensile strength of from 150 to 650, preferably 250 to 500 grams/2.5 cm, and an elongation at break of from 200 to 700 percent, preferably 250 to 500 percent.

For tape underwrap uses, the non-pressure-sensitive adhesive material is preferably provided in the same fibers as the pressure-sensitive adhesive material as blended fibers or conjugate fibers. Where the non-pressure-sensitive material is in the form of separate commingled fibers with the pressure-sensitive adhesive fibers, the resulting cohesive wrap generally has a higher tensile strength which adversely affects the tearability of the wrap making it less easy to use. The use of lower levels of commingled non-pressure-sensitive adhesive fibers would provide for lower tensile properties but higher adhesion properties making the material less dispensable or nondispensible. However, low levels of commingled fibers (e.g., 5 to 50 percent) can be used to increase tensile strengths of cohesive wrap materials formed using conjugate or blend fibers which cohesive wrap would otherwise have low strength but adequate adhesive properties.

The cohesive wrap material is generally formed into a roll form without the use of release liners or release coatings yet still results in a roll of coherent material such that can be easily dispensed without blocking, tearing, or cohesive failure (e.g., splitting of the fibrous web or wrap) of the wrap. The level of self adhesion or cohesion of the wrap material to itself must generally be significantly less than the tensile strength of the material, preferably less than the tensile strength of the material at low levels of elongation. This adhesion level is preferably measured by T-peel adhesion (as defined in the examples). The T-peel adhesion of the invention cohesive wrap generally should be from 1 to 30 grams/2.5 cm, preferably 1 to 10 grams/2.5 cm, and most preferably, 3 to 8 grams/2.5 cm. The use of higher levels of pressure-sensitive adhesive fibers resulting in T-peel adhesion can create unwanted fiber picking, cohesive failure or blocking of the wrap when on a roll without a liner or the like.

The basis weight of the wrap material is generally from 40 to 200 grams/m$^2$. For tape underwrap application, a lower basis weight is preferred, generally about 40 to 80 grams/m$^2$, more preferably 50 to 70 grams/m$^2$. A higher basis weight wrap can result in a material that is too strong for easy tearability or is to lofty or has too high of a T-peel adhesive strength.

The invention nonwoven cohesive wrap finds particular advantageous use as a protective underwrap. Generally, the protective underwrap is coherent such that it can be dispensed, wound on itself and unwound or removed without the wrap tearing, splitting, or the like. For this use, the combination of lower strength for tearability, removable self-adhesion, dispensability and without cohesive failure, breathability, adherability, and elastic properties provided by the invention cohesive wrap is unique. However, the invention cohesive wrap can also be used as a stand alone wrap for athletic or medical applications, where higher strength, higher basis weight wraps can be used advantageously. Preferably for this class of use the invention wrap will have a basis weight of from 80 to 200 grams/m², preferably 100 to 180 grams/m². At these higher basis weights, the wraps have higher strengths and therefor can have higher levels of self adhesion and still be removable. The invention cohesive wrap can also be used as a protective underwrap for orthopedic casting articles, including casts and splints.

EXAMPLES

The following examples are offered to aid in understanding of the present invention and are not to be construed as limiting the scope thereof. Unless otherwise indicated, all parts and percentages are by weight.

The following test methods were used for evaluation purposes in the examples:

Tensile Strength: ASTM Test Method No. D3759-83 using a sample width of 2.5 cm, a gauge length of 2.5 cm, and a crosshead speed of 25 cm/min. Reported is the maximum force applied to the test sample to obtain the tensile value at point of break.

Elongation at Break: ASTM Test Method No. D3759-83 using a sample width of 2.5 cm, a gauge length of 2.5 cm, and a crosshead speed of 25 cm/min. Reported is the maximum percent of stretch reached by the test sample at point of break.

Force at 50% Elongation: INDA Standard Test 90-75 (R77) using a sample width of 2.5 cm. Reported is the force applied to the test sample to obtain 50% stretch.

Recovery Force at 50% Elongation: INDA Standard Test 90-75 (R 77).

Percent (%) Recovery: INDA Standard Test 90-75 (R 77).

Adhesive Strength: T-Peel Test ("Peel Force" test as described in U.S. Pat. No. 5,531,855, which is incorporated herein by reference.)

EXAMPLE 1

A BMF-PSA web comprised of three-layer polymeric fibers was prepared using a melt blowing process similar to that described, for example, in Wente, Van A., "Superfine Thermoplastic Fibers," in *Industrial Engineering Chemistry*, Vol. 48, pages 1342 et seq (1956) or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized two extruders, each of which fed its extrudate to a gear pump that controlled the polymer melt flow. The gear pumps fed a three-layer feedblock (splitter) assembly similar to that described in U.S. Pat. Nos. 3,480, 502 (Chisholm, et al.) and 3,487,505 (Schrenk), which are incorporated herein by reference. The feedblock assembly was connected to a melt-blowing die having circular smooth surface orifices (10/cm) with a 5:1 length to diameter ratio. The primary air was maintained at 240° C. and 241 KPa with a 0.076 cm gap width to produce a uniform web. Both the die and feedblock assembly were maintained at 240° C., and the die was operated at a rate of 178 g/hr/cm die width.

The feedblock assembly was fed by two polymer melt streams, one being a melt stream of EASTOFLEX™ D-127S polyalphaolefin PSA (Eastman Chemical Co., Kingsport, Tenn.) at 200° C., and the other being a melt stream of EXACT™ 4023 metallocene polyethylene resin Exxon Chemicals, Houston, Tex.) at 240° C. The gear pumps were adjusted to produce a 15/85 ratio of poly alpha olefin PSA to polyethylene resin (based on a pump ratio percent), and the BMF-PSA web was collected on a double coated silicone release paper (Daubert Coated Products, Westchester, Ill.) which passed around a rotating drum collector at a collector to die distance of 20.3 cm. The feedblock assembly split the melt streams and recombined them in an alternating manner into a three-layer melt stream exiting the feedblock assembly, the outermost layers of the exiting stream being the adhesive. The resulting BMF-PSA web had a basis weight of about 60 g/m².

EXAMPLE 2

A BMF-PSA web comprised of three-layer polymeric fibers was prepared essentially as described in EXAMPLE 1, except that the resulting BMF-PSA web had a basis weight of about 110 g/m².

EXAMPLE 3

A BMF-PSA web comprised of three-layer polymeric fibers was prepared essentially as described in EXAMPLE 1, except that isooctyl acrylate/acrylic acid/styrene macromer (IOA/AA/Sty, 92/4/4 ratio, Inherent Viscosity ~0.65 as measured by conventional means using a Cannon-Fenski #50 viscometer in a water bath controlled at 25° C. to measure the flow time of 10 ml of a polymer solution (0.2 g per deciliter polymer in ethyl acetate)) PSA, prepared as described in Example 2 of U.S. Pat. No. 5,648,166, which is incorporated herein by reference, was substituted for the EASTOFLEX™ D-127S polyalphaolefin PSA and KRATON™ G-1657 resin, a hydrogenated styrene/ethylene-butylene/styrene A-B-A block copolymer (Shell Chemical Corp., Houston, Tex.) was substituted for the EXACT™ 4023 polyethylene resin. The gear pumps were adjusted to produce a 30/70 ratio of IOA/AA/Sty PSA/KRATON™ G-1657 resin with the outer most layers of the exiting stream being the PSA. The resulting BMF-PSA web had a basis weight of about 66 g/m².

EXAMPLE 4

A BMF-PSA web comprised of three-layer polymeric fibers was prepared essentially as described in EXAMPLE 1, except that a 50/50 blend of EXACT™ 4023 metallocene polyethylene resin and MORTHANE™ PS-440-200 polyurethane resin (Morton Thiokol Corporation, Seabrook, N.H.) was substituted for the EXACT™ 4023 polyethylene resin. The gear pumps were adjusted to produce a 15/85 ratio of polyalphaolefin PSA to polyethylene/polyurethane resin with the outer most layers of the exiting stream being the adhesive. The resulting BMF-PSA web had a basis weight of about 62 g/m².

EXAMPLE 5

A BMF-PSA web comprised of three-layer polymeric fibers was prepared essentially as described in EXAMPLE 1, except that the IOA/AA/Sty PSA was substituted for the EASTOFLEX™ D-127S polyalphaolefin PSA. The gear pumps were adjusted to produce a 17/83 ratio of PSA to polyethylene resin with the outer most layers of the exiting stream being the PSA. The resulting BMF-PSA web was collected at a collector to die distance of 23 cm and had a basis weight of about 66 g/m².

EXAMPLE 6

A BMF-PSA web comprised of three-layer polymeric fibers was prepared essentially as described in EXAMPLE 1, except that Tackified Block Copolymer HL-2547 PSA (H.

B. Fuller Company, St. Paul, Minn.) was substituted for the EASTOFLEX™ D-127S polyalphaolefin PSA. The gear pumps were adjusted to produce a 17/83 ratio of PSA to polyethylene resin with the outer most layers of the exiting stream being the PSA. The resulting BMF-PSA web was collected at a collector to die distance of 23 cm and had a basis weight of about 66 g/m².

EXAMPLE 7

A BMF-PSA web comprised of single-layer blended polymeric fibers was prepared essentially as described in EXAMPLE 1, except that the BMF apparatus utilized one conical twin-screw extruder which was used to blend the different polymers. The extruder, the feedblock assembly and the melt-blowing die were maintained at 220° C. The primary air was maintained at 220° C. and 138 Kpa with a 0.076 cm gap width, to produce a uniform web.

The feedblock assembly was fed by a polymer melt stream comprised of a uniform blend of 40% EASTOFLEX™ D-127S polyalphaolefin PSA and 60% EXACT™ 4023 metallocene polyethylene resin. The BMF-PSA web was collected on a double coated silicone release paper which passed around a rotating drum collector at a collector to die distance of 24 cm. The resulting BMF-PSA web had a basis weight of about 61 g/m².

EXAMPLE 8

A BMF-PSA web comprised of single-layer blended polymeric fibers was prepared essentially as described in EXAMPLE 7, except that the resulting BMF-PSA web had a basis weight of about 91 g/m².

EXAMPLE 9

A BMF-PSA web comprised of single-layer blended polymeric fibers was prepared essentially as described in EXAMPLE 7, except that the polymer blend was comprised of 50% Tackified Block Copolymer HL-2547 PSA and 50% EXACT™ 4023 metallocene polyethylene resin. The resulting BMF-PSA web had a basis weight of about 65 g/m².

EXAMPLE 10

A BMF-PSA web comprised of commingled single-layer polymeric fibers was prepared using a melt blowing process similar to that described in U.S. Pat. No. 3,971,373 (Braun), which is incorporated herein by reference, except that no particles were loaded into the commingled web, the two melt blowing dies had circular smooth orifices (10/cm) with a 5:1 length to diameter ratio, the dies were configured at about 15 degrees from horizontal, and the collector was located about 20 cm form the die orifices.

One of the extruders delivered a stream of IOA/AA/Sty PSA at 224° C. and a rate of 1200 g/hr/cm die width, to a BMF die which was maintained at 220° C. The primary air for this die was maintained at 240° C. and 138 Kpa with a 0.076 cm gap width. A second extruder delivered a stream of MORTHANE™ PS-440-200 polyurethane resin at 218° C. and a rate of 2400 g/hr/cm die width, to a second BMF die, which was maintained at 225° C. The primary air for the second die was maintained at 240° C. and 138 Kpa with a 0.076 cm gap width. The BMF-PSA web was collected on a double coated silicone release paper which passed around the rotating drum collector. The resulting substantially symmetrically commingled IOA/AA/Sty PSA (33%)/polyurethane resin (67%) BMF-PSA web had a basis weight of about 160 g/m².

EXAMPLE 11

A BMF-PSA web comprised of commingled single-layer polymeric fibers was prepared essentially as described in EXAMPLE 10, except that EASTOFLEX™ D-127S polyalphaolefin PSA was substituted for the IOA/AA/Sty PSA and ESCORENE™ 3795 polypropylene resin (Exxon Chemicals, Houston, Tex.) was substituted for the MORTHANE™ PS-440-200 polyurethane resin. The resulting substantially symmetrically commingled polyalphaolefin PSA (33%)/polypropylene resin (67%) BMF-PSA web had a basis weight of about 50 g/m².

EXAMPLE 12

A BMF-PSA web comprised of commingled single-layer polymeric fibers was prepared as described in EXAMPLE 10, except that EASTOFLEX™ D-127S polyalphaolefin PSA was substituted for the IOA/AA/Sty PSA and PET 651000 polyester resin (3M Company, St. Paul, Minn.) was substituted for the MORTHANE™ PS-440-200 polyurethane resin. The resulting substantially symmetrically commingled polyalphaolefin PSA (25%)/polyester resin (75%) BMF-PSA web had a basis weight of about 51 g/m².

EXAMPLE 13

A BMF-PSA web comprised of commingled single-layer polymeric fibers was prepared as described in EXAMPLE 10, except that EASTOFLEX™ D-127S polyalphaolefin PSA was substituted for the IOA/AA/Sty PSA and ULTRAMID™ B-3S polyamide resin (BASF, Parsippany, N.J.) was substituted for the MORTHANE™ PS-440-200 polyurethane resin. The resulting substantially symmetrically commingled polyalphaolefin PSA (50%)/polyamide resin (50%) BMF-PSA web had a basis weight of about 51 g/m².

TEST DATA

The BMF-PSA web samples from the above examples were cut into tape samples and evaluated (Machine Direction) for Tensile Strength, % Elongation at Break, Force at 50% Elongation, Adhesive Strength ("T-Peel"), Recovery Force at 50% Elongation, and % Recovery. Results are provided in Table 1.

TABLE 1

Physical Properties of BMF-PSA Tape Samples

| Sample (Exp.) | Tensile Strength (g/2.5 cm) | % Elongation at Break | Force at 50% Elongation (g/2.5 cm) | Adhesive Strength (g/2.5 cm) | Recovery Force at 50% Elongation (g/2.5 cm) | % Recovery |
|---|---|---|---|---|---|---|
| 1 | 270 | 305 | 210 | 4.2 | 130 | 95 |
| 2 | 410 | 355 | 340 | 5.6 | 260 | 95 |

TABLE 1-continued

Physical Properties of BMF-PSA Tape Samples

| Sample (Exp.) | Tensile Strength (g/2.5 cm) | % Elongation at Break | Force at 50% Elongation (g/2.5 cm) | Adhesive Strength (g/2.5 cm) | Recovery Force at 50% Elongation (g/2.5 cm) | % Recovery |
|---|---|---|---|---|---|---|
| 3 | 171 | 890 | 88 | 22.4 | 70 | 95 |
| 4 | 620 | 785 | 105 | 3.9 | 85 | 100 |
| 5 | 318 | 542 | 182 | 5.7 | NM[1] | NM |
| 6 | 318 | 661 | 182 | 8.5 | NM | NM |
| 7 | 249 | 630 | 160 | 2.8 | 125 | 95 |
| 8 | 365 | 600 | 265 | 3.3 | 180 | 95 |
| 9 | 354 | 790 | 145 | 0.8 | 80 | 90 |
| 10 | 2000 | 490 | 730 | 21.0 | 510 | 100 |
| 11 | 1860 | 175 | 930 | 3.5 | 70 | 45 |
| 12 | 635 | 320 | 320 | 2.8 | 120 | 70 |
| 13 | 1540 | 165 | 945 | 2.3 | 90 | 40 |

[1]NM = Not Measured

TAPE EVALUATIONS

All of the tape samples from Examples 1–13 were prepared in roll form without stretching as they were slit to width and surface wound on the score roll. No liners were utilized and blocking was not observed to be a problem. All of the samples were then evaluated under actual use conditions by evaluators familiar with wrapping tapes on various anatomical joints. No adhesives or other "skin preparation" materials were used. The tapes were supplied in roll form and were applied by the evaluators as cohesive wraps for overtaping in the usual manner. All of the tape samples unwound easily from the roll without damage, wrapped very smoothly around the limb and conformed well to the irregular surfaces and angles of the limb. When the wrapping process was completed, the tapes were easily torn off of the roll and the loose end readily adhered onto the wrapped limb. The tape samples were also used as cohesive wraps to readily affix devices, for example absorbent bandages or ice bags, onto the limb. The wraps performed this holding function very successfully.

What is claimed is:

1. A dispensable nonwoven cohesive wrap comprising a coherent self-supporting web comprising entangled pressure-sensitive adhesive fibers and a non-pressure-sensitive adhesive fibrous material, the wrap having a tensile strength of at least 100 grams/2.5 cm and a T-peel from itself from 1 to 30 grams/2.5 cm.

2. The nonwoven cohesive wrap of claim 1 wherein the wrap has an elastic recovery of at least 40 percent at an elongation of 50 percent.

3. The nonwoven cohesive wrap of claim 2 wherein the wrap has a force at 50 percent elongation of at least 75 grams/2.5 cm.

4. The nonwoven cohesive wrap of claim 3 wherein the force at 50 percent elongation is less than 1000 grams/2.5 cm.

5. The nonwoven cohesive wrap of claim 3 wherein the force at 50 percent elongation is from 150 to 200 grams/2.5 cm.

6. The nonwoven cohesive wrap of claim 3 wherein the force at 50 percent elongation is from 200 to 400 grams/2.5 cm.

7. The nonwoven cohesive wrap of claim 1 wherein the wrap has a basis weight of from 40 to 200 grams/m².

8. The nonwoven cohesive wrap of claim 7 wherein the basis weight of the wrap is from 40 to 80 grams/m².

9. The nonwoven cohesive wrap of claim 3 wherein the tensile strength of the wrap is less than 2000 grams/2.5 cm.

10. The nonwoven cohesive wrap of claim 3 wherein the tensile strength of the wrap is from 150 to 650 grams/2.5 cm.

11. The nonwoven cohesive wrap of claim 3 wherein the tensile strength of the wrap is from 250 to 400 grams/2.5 cm and wherein the wrap has a basis weight of from 50 to 80 grams/m².

12. The nonwoven cohesive wrap of claim 3 wherein the wrap has an elongation at break of from 100 to 900 percent.

13. The nonwoven cohesive wrap of claim 3 wherein the wrap has an elongation at break of from 200 to 700 percent.

14. The nonwoven cohesive wrap of claim 3 wherein the wrap has an elongation at break of from 250 to 400 percent.

15. The nonwoven cohesive wrap of claim 3 wherein the wrap has an elastic recovery force of at least 50 grams/2.5 cm at 50 percent elongation.

16. The nonwoven cohesive wrap of claim 15 wherein the wrap recovers at least 80 percent at 50 percent elongation.

17. The nonwoven cohesive wrap of claim 15 wherein the wrap recovers at least 90 percent at 50 percent elongation.

18. The nonwoven cohesive wrap of claim 3 wherein the T-peel from itself is from 1 to 10 grams/2.5 cm.

19. The nonwoven cohesive wrap of claim 3 wherein the T-peel from itself is from 3.5 to 8 grams/2.5 cm.

20. The nonwoven cohesive wrap of claim 1 wherein the wrap can be readily torn by hand.

21. The nonwoven cohesive wrap of claim 1 wherein the wrap comprises commingled pressure-sensitive adhesive fibers and non-pressure-sensitive adhesive fibers.

22. The nonwoven cohesive wrap of claim 1 wherein the wrap pressure-sensitive adhesive fibers comprise a blend of a pressure-sensitive adhesive phase and a thermoplastic phase.

23. The nonwoven cohesive wrap of claim 1 wherein the pressure-sensitive adhesive fibers have two or more layers along the length of the fibers at least one layer being a pressure-sensitive adhesive layer forming at least a portion of the outer surface of the fiber and at least one second layer of a thermoplastic material.

24. The nonwoven cohesive wrap of claim 23 wherein the layers are side by side.

25. The nonwoven cohesive wrap of claim 23 wherein the layers are concentric.

26. The nonwoven cohesive wrap of claim 23 wherein the layers are coextensive and continuous along the length of the fiber.

27. The nonwoven cohesive wrap of claim 26 wherein there are at least three alternating layers.

28. The nonwoven cohesive wrap of claim 1 wherein the web is formed of melt blown pressure-sensitive adhesive fibers.

29. The nonwoven cohesive wrap of claim 1 wherein the web is formed of spunbond pressure-sensitive adhesive fibers.

30. The nonwoven cohesive wrap of claim 1 wherein the pressure-sensitive adhesive fibers have an average diameter of less than about 50 microns.

31. The nonwoven cohesive wrap of claim 1 wherein the wrap consists essentially of a single layer nonwoven web comprising the entangled pressure-sensitive adhesive fibers.

32. The nonwoven cohesive wrap of claim 1 wherein the pressure-sensitive adhesive is a tackified rubber-resin adhesive.

33. The nonwoven cohesive wrap of claim 32 wherein the tackified rubber-resin adhesive comprises an A-B type block copolymer and a compatible resin.

34. The nonwoven cohesive wrap of claim 1 wherein the pressure-sensitive adhesive comprises a polyalphaolefin.

35. The nonwoven cohesive wrap of claim 1 wherein the pressure-sensitive adhesive comprises an acrylate pressure-sensitive adhesive.

36. The nonwoven cohesive wrap of claim 1 wherein the wrap is in the form of a roll.

* * * * *